(12) United States Patent
Carroll

(10) Patent No.: US 6,380,406 B1
(45) Date of Patent: Apr. 30, 2002

(54) HOMOGENEOUS EPOXIDATION CATALYST

(75) Inventor: Kevin M. Carroll, Havertown, PA (US)

(73) Assignee: Arco Chemical Technology, L.P., Greenville, DE (US)

(*) Notice: Subject to any disclaimer, the term of this patent is extended or adjusted under 35 U.S.C. 154(b) by 22 days.

(21) Appl. No.: 09/633,525

(22) Filed: Aug. 4, 2000

(51) Int. Cl.$^7$ .......................... C07D 301/19; C07F 7/18
(52) U.S. Cl. .......................... 549/529; 556/54; 556/56; 556/460; 556/462; 556/466; 502/242
(58) Field of Search .......................... 549/529; 556/54, 556/56, 460, 462, 466; 502/242

(56) References Cited

U.S. PATENT DOCUMENTS

| | | | |
|---|---|---|---|
| 3,351,635 A | 11/1967 | Kollar | 260/348.5 |
| 4,367,342 A | 1/1983 | Wulff et al. | 549/529 |
| 5,750,741 A | 5/1998 | Crocker et al. | 549/525 |

FOREIGN PATENT DOCUMENTS

WO    WO 99/49972    10/1999

OTHER PUBLICATIONS

Winkhofer, et al., *Angew. Chem., Int. Ed. Eng.* (1994) 33, No. 13, pp 1352–1354.

Feher, et al., *Organometallics* (1991) 10, 2526–2528.

*Primary Examiner*—Ba K. Trinh
(74) *Attorney, Agent, or Firm*—Kevin M. Carroll

(57) ABSTRACT

A process for forming an olefin epoxidation catalyst is described. The process comprises reacting a tert-alkyl trihydroxysilane with a titanium complex such that the ratio of Si:Ti is 7. The catalyst is very active and selective in olefin epoxidation.

12 Claims, No Drawings

HOMOGENEOUS EPOXIDATION CATALYST

FIELD OF THE INVENTION

This invention relates to a method of producing an improved titanium-containing catalyst and its use in an epoxidation process. The catalyst is obtained by reacting a tert-alkyl trihydroxysilane with a titanium complex. The method is a simple procedure to form soluble catalysts from commercially available reagents. The catalyst is highly active for olefin epoxidation.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethyl benzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342.

Catalyst improvements are desired for this commercially practiced technology. U.S. Pat. No. 5,750,741 discloses the use of soluble titanasilsesquioxanes in the epoxidation of olefins. The homogeneous titanasilsesquioxane catalysts are taught as highly active and selective catalysts when compared to solubilized molybdenum. PCT Intl. Appl. No. WO 99/49972 also discloses that these titanasilsesquioxanes are useful as activators for deactivated heterogeneous titania on silica catalysts.

One potential disadvantage of these new homogeneous catalysts is the difficulty in preparing the titanasilsesquioxanes. The catalysts require the initial preparation of an incompletely condensed silsesquioxane $[R_7Si_7O_9(OH)_3]$ which is described in U.S. Pat. No. 5,750,741 as taking from greater than five days, when R is cyclopentyl, to greater than six months, when R is cyclohexyl. Feher, et al., *Organometallics* (1991) 10, 2526, also describe the synthesis of incompletely condensed silsesquioxane in low yield taking from more than seven days, when R=cyclopentyl, to greater than six weeks, when R=cycloheptyl.

Due to the difficulty in forming the incompletely condensed precursor, a new method for forming active homogeneous titanium catalysts would be worthwhile. Winkhofer, et al., *Angew. Chem. Int. Ed. Eng.* (1994) 33, 1352, describe the formation of titanasilsesquioxanes having a 1:1 Si:Ti ratio from stabilized silanetriols. Winkhofer also describes that for the reaction of silanetriol t-BuSi(OH)$_3$, it proved advantageous to use SnMe$_3$ protecting groups.

In sum, new olefin epoxidation catalysts and new processes to form them are needed. Particularly valuable would be processes that form high activity and high selectivity catalysts in simple, timely steps.

SUMMARY OF THE INVENTION

The invention is a method of producing an olefin epoxidation catalyst. The method comprises reacting a trihydroxysilane having the chemical formula $R^1R^2R^3C$—Si(OH)$_3$ with a titanium complex having the chemical formula TiL$_n$, wherein $R^1$, $R^2$, and $R^3$ are the same or different C$_1$–C$_{10}$ hydrocarbyl, n is 3 or 4, and L is halide, alkoxide, 2,4-alkanedionate, silyloxide, amide, cyclopentadienyl, hydrocarbyl, or mixtures thereof. The ratio of the $R^1R^2R^3C$—Si(OH)$_3$:TiL$_n$ is seven.

We surprisingly found that the new method produces catalysts that are active and selective in olefin epoxidation and are made in a much simpler process than previous prior art methods.

DETAILED DESCRIPTION OF THE INVENTION

The method of the invention comprises reacting a trihydroxysilane, substituted with a tertiary alkyl group, with a titanium complex so that the Si:Ti ratio is 7:1. It is surprisingly found that the tertiary alkyl substituent is necessary in order to produce catalysts with high activity and selectivity in olefin epoxidation compared to secondary and linear alkyls (see Table 1). The Si:Ti ratio is also unexpectedly important in forming active and selective catalysts (see Table 2).

The trihydroxysilane has the chemical formula $R^1R^2R^3C$—Si(OH)$_3$, wherein $R^1$, $R^2$, and $R^3$ are the same or different C$_1$–C$_{10}$ hydrocarbyl group. Preferably, $R^1$, $R^2$, and $R^3$ are the same or different C$_1$–C$_4$ alkyl or a C$_6$–C$_{10}$ aryl group. Particularly preferred trihydroxysilanes include t-butyl trihydroxysilane and t-amyl trihydroxysilane.

The titanium complex has the formula TiL$_n$, wherein n is 3 or 4 and L is halide, alkoxide, 2,4-alkanedionate, silyloxide, amide, cyclopentadienyl, hydrocarbyl, or mixtures thereof. Preferably, the titanium complexes include chloride, bromide, iodide, ethoxide, isopropoxide, acetylacetonate (2,4-pentanedionate), trimethylsiloxide, dimethyl amide, diethyl amide, cyclopentadienyl, or benzyl substituents. Most preferably, the titanium complex is titanium(IV) isopropoxide, titanium(IV) chloride, or tetrabenzyltitanium.

The reaction of trihydroxysilane and titanium complex is preferably performed in a solvent. Suitable solvents include any known hydrocarbons, oxygenated hydrocarbons, and halogenated hydrocarbons. Examples of suitable solvents include toluene, n-hexane, n-heptane, cyclopentane, ethanol, isopropanol, diethyl ether, acetone, methylene chloride, chloroform, chlorobenzene, and the like.

The product of the reaction is typically a solid compound. The product is preferably purified by any suitable purification method before use. Preferably, the product is purified by crystallization. Crystallization methods are well known in the art.

The trihydroxysilane is prepared by any suitable method. Preferably, the trihydroxysilane is formed by the hydrolysis of a trihalosilane. The trihalosilane compound has the chemical formula $R^1R^2R^3C$—SiX$_3$, wherein $R^1$, $R^2$, and $R^3$ are the same or different C$_1$–C$_{10}$ hydrocarbyl group and X is a halide. Preferred halides include chlorine and bromine. In the hydrolysis reaction, the trihalosilane is reacted with water, preferably in a H$_2$O:$R^1R^2R^3C$—SiX$_3$ ratio of 3:1 to allow formation of the trihydroxysilane with no excess water. Because hydrohalic acid, HX, is formed during the hydrolysis of trihalosilane, a basic compound is typically added to the reaction mixture. The basic compound reacts with HX to form a stable base.HX salt that is readily separated from the trihydroxysilane product. Although any basic compound that forms a stable salt with HX is suitable, preferred basic compounds include aliphatic and aromatic amines, particularly ethylamine, diethylamine, triethylamine, pyridine, aniline, piperidine, and the like.

The epoxidation process of the invention comprises contacting an olefin with an organic hydroperoxide in the presence of the catalyst of the invention. Suitable olefins include any olefin having at least one carbon-carbon double bond, and generally from 2 to 60 carbon atoms. Preferably the olefin is an acyclic alkene of from 3 to 10 carbon atoms such as propylene, butene, pentene, hexene, heptene, octene, nonene, decene, and isomers thereof. Also preferred are olefinically unsaturated compounds substituted with a hydroxyl group or a halogen group such as allyl chloride or allyl alcohol. Particularly preferred olefin is propylene.

Preferred organic hydroperoxides are hydrocarbon hydroperoxides having from 3 to 20 carbon atoms. Particularly preferred are secondary and tertiary hydroperoxides of from 3 to 15 carbon atoms, especially secondary alkyl hydroperoxides wherein the hydroperoxy group is on a carbon atom attached directly to an aromatic ring, e.g., ethylbenzene hydroperoxide. Other exemplary organic hydroperoxides suitable for use include t-butyl hydroperoxide, t-amyl hydroperoxide, cyclohexyl hydroperoxide, and cumene hydroperoxide.

In such an epoxidation process the olefin:hydroperoxide molar ratio is not particularly critical, but it is preferable to employ a molar ratio of from 1:1 up to 20:1.

The epoxidation reaction is conducted in the liquid phase in solvents or diluents that are liquid at the reaction temperature and pressure and are substantially inert to the reactants and the products produced therefrom. In commercial practice, it will generally be most economical to use as a solvent the hydrocarbon used to produce the organic hydroperoxide reactant. For example, when ethylbenzene hydroperoxide is utilized, the use of ethylbenzene as the epoxidation solvent is preferred. It is conducted at moderate temperatures and pressures. Typically, the organic hydroperoxide is present at concentrations of from about 1 to 50 percent by weight of the epoxidation reaction mixture (including olefin). Suitable reaction temperatures vary from 0° C. to 200° C., but preferably from 25° C. to 150° C. The reaction is preferably conducted at or above atmospheric pressure. The precise pressure is not critical. The reaction mixture may, for example, be maintained substantially in a non-gaseous phase or as a two-phase (gas/liquid) system. The catalyst formed by the reaction of trihydroxysilane and titanium complex is soluble and thus is present in the liquid phase during the epoxidation process of this invention. Typical pressures vary from 1 atmosphere to 100 atmospheres.

The epoxidation may be performed using any of the conventional reactor configurations known in the art for reacting olefin and organic hydroperoxide in the presence of a soluble catalyst. Continuous as well as batch procedures may be used. The reaction solvent, the catalyst, and any unreacted olefin or organic hydroperoxide may be recycled for further utilization.

The following examples merely illustrate the invention. Those skilled in the art will recognize many variations that are within the spirit of the invention and scope of the claims.

EXAMPLE 1

This example describes the preparation of Catalyst 1 by the reaction of t-butyltrihydroxy silane with titanium (isopropoxide).

Aniline (35.7 mL, 36.5 g, Acros product) and deionized water (7.1 g) are dissolved in 1.5 L of anhydrous diethyl ether and cooled in an ice bath. T-butyltrichlorosilane (25 g, Aldrich 96%) is dissolved in 100 mL of anhydrous diethyl ether in a dropping funnel and is then added dropwise to the aniline/water mixture. The reaction mixture is stirred overnight, allowing to warm to room temperature. White solids of aniline.HCl are then filtered off leaving an ether filtrate. The ether is removed by vacuum distillation until approximately 200 mL of the ether remains. The t-butyltrihydroxysilane precipitates from the concentrated solution and is then removed by filtration and dried. The isolated t-butyltrihydroxysilane (12.9 g, 73% yield) is used in the next step.

T-butyltrihydroxysilane (1.5 g) is weighed into a 3-neck round-bottom flask that is connected to an inert gas inlet and a water-cooled reflux condenser. Toluene (40 mL) is added to the flask, followed by Ti($^i$OPr)$_4$ (0.51 mL, Si:Ti=7). The mixture is refluxed for 4 hours, cooled to room temperature, and toluene removed by vacuum distillation. The oily reaction product is recrystallized from pentane to give Catalyst 1.

COMPARATIVE EXAMPLE 2

This example describes the preparation of Comparative Catalyst 2 from trichloro-3-chloropropylsilane.

Aniline (35.7 mL, 36.5 g, Acros product) and deionized water (7.1 g) are dissolved in 1.5 L of anhydrous diethyl ether and cooled in an ice bath. Trichloro-3-chloropropylsilane (27.7 g, Aldrich 97%) is dissolved in 100 mL anhydrous diethyl ether in a dropping funnel and is then added dropwise to the aniline/water mixture. The reaction mixture is stirred overnight, allowing to warm to room temperature. White solids of aniline.HCl are then filtered off leaving an ether filtrate. The ether is removed by vacuum distillation until approximately 50 mL of the ether remains. The 3-chloropropyltrihydroxysilane product is precipitated by addition of pentane.

3-chloropropyltrihydroxysilane (2 g) is weighed into a 3-neck round-bottom flask that is connected to an inert gas inlet and a water-cooled reflux condenser. Toluene (40 mL) is added to the flask, followed by Ti($^i$OPr)$_4$ (0.54 mL, Si:Ti=7). The mixture is refluxed for 4 hours, cooled to room temperature, and toluene is removed by vacuum distillation. The oily reaction product is recrystallized from diethyl ether to give Comparative Catalyst 2.

COMPARATIVE EXAMPLE 3

This example describes the preparation of Comparative Catalyst 3 from trichlorocyclopentylsilane.

Aniline (13.4 mL, 13.7 g, Acros product) and deionized water (2.65 g) are dissolved in 110 mL of anhydrous toluene in a 250 mL round-bottom flask and cooled in an ice bath. Trichlorocyclopentylsilane (10 g, Aldrich 97%) is dissolved in 40 mL of anhydrous toluene in a dropping funnel and is then added dropwise to the aniline/water mixture. The reaction mixture is allowed to warm to room temperature and the aniline.HCl is filtered off leaving a toluene filtrate. The toluene solution is added to a 250 mL round bottom flask.

Titanium isopropoxide (Ti($^i$OPr)$_4$, 1.9 mL, Si:Ti=7) is then added to the toluene solution. The mixture is refluxed for 4 hours, cooled to room temperature, and the toluene is removed by vacuum distillation. The oily reaction product is recrystallized from diethyl ether to give Comparative Catalyst 3.

COMPARATIVE EXAMPLE 4

This example describes the preparation of Comparative Catalyst 4 from phenyltrichlorosilane.

Aniline (12.9 mL, 13.2 g, Acros product) and deionized water (2.6 g) are dissolved in 110 mL of anhydrous diethyl ether in a 250 mL round-bottom flask and cooled in an ice bath. Phenyltrichlorosilane (10 g, Aldrich 97%) is dissolved in 40 mL anhydrous toluene in a dropping funnel and is then added dropwise to the aniline/water mixture. The reaction mixture is allowed to warm to room temperature and the aniline.HCl is filtered off leaving a toluene filtrate. The toluene solution is added to a 250 mL round bottom flask. Titanium isopropoxide (Ti($^i$OPr)$_4$, 1.99 mL, Si:Ti=7) is then added to the toluene solution. The mixture is refluxed for 4 hours, cooled to room temperature, and the toluene is removed by vacuum distillation. The oily reaction product is recrystallized from pentane to give Comparative Catalyst 4.

COMPARATIVE EXAMPLE 5

This example describes the preparation of Comparative Catalysts 5A and 5B.

Catalysts 5A and 5B are prepared according to Example 1, except that 5A uses 1.18 mL Ti($^i$OPr)$_4$ for a Si:Ti ratio of 3:1 and 5B uses 3.56 mL Ti($^i$OPr)$_4$ for a Si:Ti ratio of 1:1.

EXAMPLE 6: BATCH EPOXIDATION OF 1-OCTENE

This example describes the batch epoxidation of 1-octene with EBHP using the catalysts of Example 1 and Comparative Catalysts 2–5B:

A mixture containing 17.0 g 1-octene, 10 g EBHP oxidate and 1 g nonane (as internal standard) is added to a 4-neck round bottom flask charged with a condenser, a thermocouple, gas inlet, a stir bar and a sampling port. A sample for GC analysis was taken after the reaction mixture was stirred thoroughly under inert atmosphere. The mixture is heated to 100° C. and catalyst (~0.012 g) is then added to the flask. The reaction is run for one hour at 100° C., after which a liquid sample is taken for product GC analysis. The results are shown in Tables 1 and 2.

The results show that a tertiary alkyl group is necessary in order to produce catalysts with high activity and selectivity in olefin epoxidation (see Table 1). Comparable catalysts produced with secondary and linear alkyls give much lower conversion and selectivity under the same conditions. Table 2 demonstrates that the Si:Ti ratio is also an unexpectedly important factor in forming an active and selective catalyst (see Table 2). A Si:Ti ratio of 7 is shown to produce catalysts with both high activity and selectivity compared to the procedures where the Si:Ti ratio is lower (see Table 2).

TABLE 1

Effect of Trihydroxysilane Substituent on Olefin Epoxidation

| Catalyst | Substituent | Conversion (%) | Selectivity (%) |
|---|---|---|---|
| 1 | t-butyl | 68 | 93 |
| 2* | 3-chloropropyl | 10 | 52 |
| 3* | c-pentyl | 17 | 46 |
| 4* | Phenyl | 41 | 86 |

*Comparative Example.

TABLE 2

Effect of Si:Ti Ratio on Olefin Epoxidation

| Catalyst | Si:Ti | Conversion (%) | Selectivity (%) |
|---|---|---|---|
| 1 | 7 | 68 | 93 |
| 5A* | 3 | 45 | 83 |
| 5B* | 1 | 50 | 74 |

*Comparative Example.

I claim:

1. A method for preparing a catalyst comprising reacting a trihydroxysilane having the formula $R^1R^2R^3C$—$Si(OH)_3$, with a titanium complex having the formula $TiL_n$, wherein $R^1$, $R^2$, and $R^3$ are the same or different $C_1$–$C_{10}$ hydrocarbyl, n is 3 or 4, L is halide, alkoxide, 2,4-alkanedionate, silyloxide, amide, cyclopentadienyl, hydrocarbyl, or mixtures thereof, and the ratio of $R^1R^2R^3C$—$Si(OH)_3$:$TiL_n$ is 7:1.

2. The method of claim 1 wherein $R^1$, $R^2$, and $R^3$ are the same or different $C_1$–$C_4$ alkyl or $C_6$–$C_{10}$ aryl.

3. The method of claim 1 wherein the trihydroxysilane is selected from the group consisting of t-butyl trihydroxysilane and t-amyl trihydroxysilane.

4. The method of claim 1 wherein L is selected from the group consisting of chloride, bromide, iodide, ethoxide, isopropoxide, acetylacetonate, trimethylsiloxide, dimethyl amide, diethyl amide, cyclopentadienyl, and benzyl.

5. The method of claim 1 wherein the titanium complex is selected from the group consisting of titanium(IV) isopropoxide, titanium(IV) chloride, and tetrabenzyltitanium.

6. The method of claim 1 wherein the trihydroxysilane is formed by reacting water, a basic compound, and a trihalosilane having the chemical formula $R^1R^2R^3C$—$SiX_3$, wherein X is a halide.

7. The method of claim 6 wherein X is a chloride.

8. The method of claim 6 wherein the basic compound is an aliphatic or aromatic amine.

9. The method of claim 8 wherein the basic compound is selected from the group consisting ethylamine, diethylamine, triethylamine, pyridine, aniline, and piperidine.

10. An epoxidation process comprising contacting an organic hydroperoxide with an olefin in the presence of the catalyst produced by the method of claim 1.

11. The epoxidation process of claim 10 wherein the organic hydroperoxide is ethylbenzene hydroperoxide or t-butyl hydroperoxide.

12. The epoxidation process of claim 10 wherein the olefin is a $C_3$–$C_{10}$ acyclic alkene.

* * * * *